United States Patent
Bramfitt et al.

[11] Patent Number: 5,935,135
[45] Date of Patent: Aug. 10, 1999

[54] BALLOON DELIVERY SYSTEM FOR DEPLOYING STENTS

[75] Inventors: John Bramfitt, Woodside; Bruce Addis, South San Francisco, both of Calif.

[73] Assignee: United States Surgical Corporation, Norwalk, Conn.

[21] Appl. No.: 08/862,422

[22] Filed: May 23, 1997

Related U.S. Application Data

[63] Continuation of application No. 08/537,122, Sep. 29, 1995, abandoned.

[51] Int. Cl.⁶ .................................................... A61F 11/00
[52] U.S. Cl. ........................ 606/108; 606/191; 606/192; 606/194
[58] Field of Search ................................. 606/191, 192, 606/194, 198; 623/1, 12; 604/96, 108

[56] References Cited

U.S. PATENT DOCUMENTS

| | | | |
|---|---|---|---|
| 4,950,227 | 8/1990 | Savin et al. | 623/1 |
| 5,019,042 | 5/1991 | Sahota | 606/194 |
| 5,108,416 | 4/1992 | Ryan et al. | 606/194 |
| 5,219,355 | 6/1993 | Parodi et al. | 606/194 |
| 5,221,261 | 6/1993 | Termin et al. | 606/194 |
| 5,352,199 | 10/1994 | Tower | 606/194 |
| 5,423,745 | 6/1995 | Todd et al. | 604/96 |
| 5,445,646 | 8/1995 | Euteneuer et al. | 604/96 |
| 5,458,605 | 10/1995 | Klemm | 606/194 |
| 5,534,007 | 7/1996 | St. Germain et al. | 606/108 |
| 5,653,690 | 8/1997 | Booth et al. | 606/194 |

*Primary Examiner*—Michael Powell Buiz
*Assistant Examiner*—Daphna Shai

[57] ABSTRACT

A balloon delivery system for deploying stents including a balloon catheter, and a stent fixedly positioned on the balloon portion of the balloon catheter by at least one protrusion such as annular cuff formed around the balloon. The balloon can include two or more continuous or discontinuous cuffs formed along the balloon which maintain one or more stents in position on the balloon. The protrusion can be created from excess material of the balloon which is configured in a desired fashion around the balloon to form the protrusion. The protrusion improves the fixation of the stent on the balloon catheter until the balloon is inflated to deploy the stent within a body lumen. The protrusion restrains the movement of the stent without a significant change in the overall profile of the balloon delivery system. The protrusion or protrusions can be provided as a series of circumferentially spaced-apart projections, a C-shaped annular cuff, a continuous annular cuff or two or more axially spaced-apart projections or cuffs.

26 Claims, 3 Drawing Sheets

BALLOON DELIVERY SYSTEM FOR DEPLOYING STENTS

This application is a continuation of application Ser. No. 08/537,122, filed Sep. 29, 1995 now abn.

BACKGROUND OF THE INVENTION

1. Field of the Invention

The present invention relates to a balloon catheter and a method of deploying stents, and more particularly, to a balloon catheter delivery system for delivering and deploying stents within a tubular organ of the body and a method of deploying stents employing the balloon catheter delivery system.

2. Description of the Related Art

Conventionally, expandable devices, called stents, are used to maintain the inner diameter of a body lumen such as an artery. Although stents are most commonly used after angioplasty, to maintain vascular patency and help in the prevention of restenosis, stents may also be used for repair of aneurysms, stabilization of interior vessel tubes such as bronchial tubes, retention of emboli and plaque, and prevention of vessel collapse. The stents are placed at a desired location within a body lumen through a guide catheter or similar device and are expanded, by various known methods, within the lumen until they are opposed to the walls of the lumen at a preferred diameter.

According to one conventional procedure for installation of stents, a stent is positioned over an inflatable portion of a catheter, such as an angioplasty catheter balloon, which is inserted into a body lumen to a position where it is desired to place the stent. Fluoroscopy, and/or other conventional techniques may be utilized to ensure that the catheter and the stent are delivered to the desired location. The stent is then expanded radially outward by inflating the expandable portion of the balloon catheter until the stent is in contact with the walls of the lumen. After the desired expansion has been accomplished, the balloon is collapsed, or deflated, and the balloon catheter is removed from the lumen.

A substantial difficulty with the conventional method of deploying a stent is the tendency for movement of the stent on the balloon. The movement of the stent on the balloon provides a potential for embolism, non-uniform expansion of the stent and the inability to retract the stent if necessary. Proposed solutions to this problem include providing a tubular protective sheath over the stent to secure the stent in place. Once the stent is in the proper position, the sheath is removed to expose the stent. The use of a sheath is disclosed in U.S. Pat. Nos. 5,158,548 and 5,102,417. Protective sheaths have drawbacks in that the sheath is bulky, the stent is not secured to the balloon under the sheath, and once the sheath is deployed the stent is not secure for further positioning. Therefore, once the sheath is removed, the stent cannot be retracted from the body on the uninflated balloon.

Another proposed solution to the problem of movement of the stent is the use of machine crimping to fix the stent on the balloon. The crimping of portions of a stent provides friction between the stent and the balloon which prevents the stent from sliding off the balloon. The use of machine crimping is discussed in U.S. Pat. No. 4,969,458. This method, however, may tear or puncture the balloon and will tend to make the stent stiff and difficult to insert.

A third proposed solution to the problem of movement of the stent is the use of an adhesive to bond the stent to the balloon. However, the use of adhesive is relatively unreliable and may create problems due to loose particles of adhesive which contaminate the surgical site. Other stent insertion catheters having means for retaining the stents on the catheters prior to deployment are disclosed in U.S. Pat. Nos. 4,969,890 and 5,102,417.

SUMMARY OF THE INVENTION

The present invention improves the fixation of a stent on a balloon catheter used to deploy the stent, by providing one or more protrusions which restrain movement of the stent without a significant change in the overall profile of the balloon delivery system. The present invention eliminates many of the disadvantages of the known methods of fixing stents in that the stent is secured to the balloon without damage to the balloon, without biocompatability problems associated with use of an adhesives, and without the retractability problems of a sheath.

In accordance with the invention, a balloon delivery system for deploying a stent within a tubular body organ includes an expandable balloon configured to receive a stent for maintaining an inside diameter of a lumen and a passage in fluid communication with the expandable balloon. The expandable balloon is provided with one or more protrusions formed on an exterior of the balloon for securing the stent on the balloon during delivery and deployment of the stent within the lumen. The protrusion may also be in the form of a continuous or discontinuous annular cuff, single projection or a series of spaced-apart projections in a circumferential array.

In accordance with another aspect of the invention, a balloon delivery system includes an expandable balloon, a substantially cylindrical, expandable stent positioned on the balloon, a tube connected to the balloon for inflating the balloon, and at least one protrusion formed on an exterior of the balloon for securing the stent on the balloon.

In accordance with another aspect of the invention, a method of deploying a stent within a body lumen with a balloon catheter is disclosed. The balloon catheter includes a balloon having at least one protrusion cooperating with the stent for securing the stent in place on the balloon. The method includes the steps of positioning a stent on the balloon catheter, inserting the balloon catheter and stent into a body through a tubular catheter, positioning the stent within a body lumen, deploying the stent by inflating the balloon, deflating the balloon, and removing the balloon and the catheter from the body.

In accordance with another aspect of the invention, a balloon delivery system for deploying a stent within a tubular body lumen comprises an expandable balloon having at least one protrusion formed on an exterior of the balloon and an articulated expandable stent positioned on the balloon. The stent includes two substantially cylindrical stent portions connected by a bridge element.

BRIEF DESCRIPTION OF THE DRAWING FIGURES

The invention will be described in greater detail with reference to the accompanying drawings in which like elements bear like reference numerals, and wherein.

DETAILED DESCRIPTION OF THE INVENTION

The invention provides an improved stent delivery system. Advantages associated with the delivery system of the invention include good stent security on the delivery system, reduced need for visibility of the stent, good pushability of the delivery system, good trackability of the delivery system, and unimpaired flexibility of the stent due to freefloating of the stent on the balloon. The need for visibility of the stent by fluoroscopy equipment is reduced due to the fact that the stent is secured in a known position on the balloon and the position of the balloon is known by reference to radiopaque markers. The pushability/trackability is provided by the catheter design and materials used for the catheter. The flexibility of the stent, i.e., ability to navigate bends in a body lumen, is provided by the inherent property of the stent design which is not compromised by the delivery system which ensures stent security.

In the inventive delivery system, stent security is provided by one or more protrusions such as one or more circumferentially spaced apart projections, continuous or discontinuous annular cuff or other suitably shaped member which prevents the stent from sliding axially off of the balloon during delivery or withdrawal of the stent to or from a particular location in a body lumen. The protrusion allows the stent to be held without crimping the stent onto the balloon. The protrusion or protrusions are preferably formed from thin plastic of the balloon material so as to provide a soft and flexible anchor at each end of the stent. As such, the protrusion or protrusions do not interfere with trackability and pushability of the delivery system.

Due to the protrusion design, upon inflation of the balloon, the protruding configuration of the protrusion is changed to a non-protruding configuration and upon deflation of the balloon, the protrusion retains the non-protruding configuration. Thus, the protrusion effectively retains the stent in position upon deployment of the stent but does not interfere with the stent upon deflation of the balloon.

Figure 1:
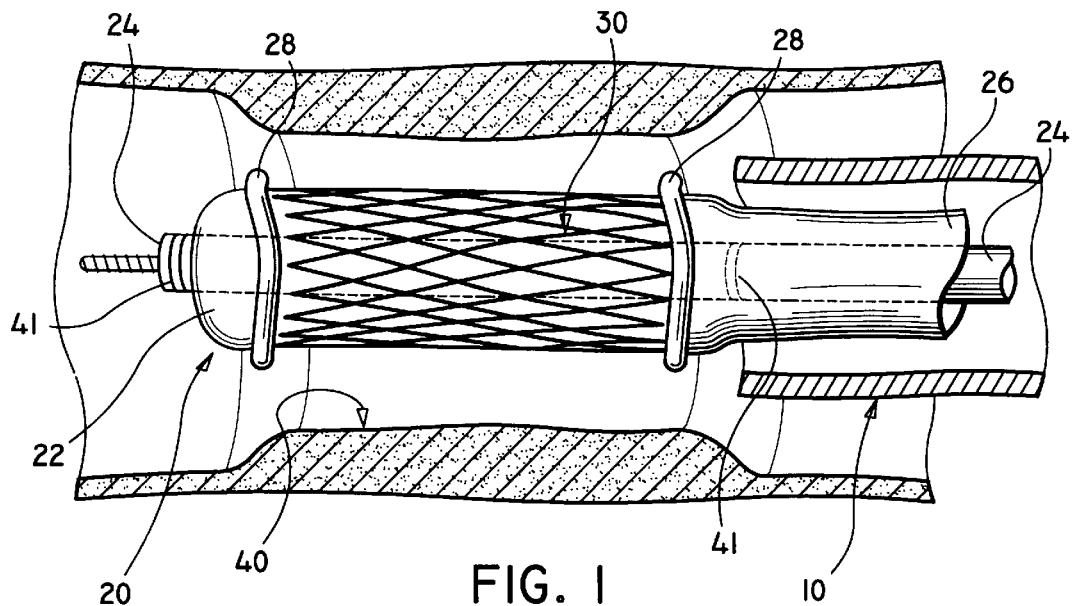
FIG. 1 is a side view, partly in section, of a balloon delivery system, according to a first embodiment of the present invention.

The balloon delivery system for deploying balloon expandable stents (e.g., stainless steel, shape memory alloy, tantalum, etc.), as shown in FIG. 1, includes an introducing catheter 10, a balloon catheter 20, and a stent 30 positioned on the balloon catheter. The balloon catheter 20 includes an expandable balloon 22 connected to a coaxial conduit having an inner conduit 24 for introduction of a guidewire and an outer conduit 26 for introduction of balloon inflation medium. The balloon 22 includes protrusions in the form of two cuffs 28 formed at either end of the balloon which maintain the stent 30 in position on the balloon. The cuffs 28 are preferably created from excess material of the balloon 22 which is configured circumferentially around the balloon to form each annular protrusion.

The balloon 22 is illustrated in the figures as positioned on the end of an over-the-wire catheter, however, the present invention can be employed in connection with a rapid exchange catheter design, a fixed wire catheter or any other known catheter design.

The balloon 22, shown in a deflated state in FIG. 1, has a cylindrical profile. However, the actual deflated balloon 22 includes numerous folds which allow the balloon material to be compressed into a tightly wound configuration for application of the stent. The folding of the balloon 22 may be performed by any one of the known methods. When the balloon 22 is inflated by introduction of an inflation medium through the outer conduit 26, the balloon expands and the folds disappear. The inner conduit 22, as illustrated in FIG. 1, preferably includes radiopaque markers 41 positioned to show the ends of the balloon under fluoroscopy.

Figure 2:
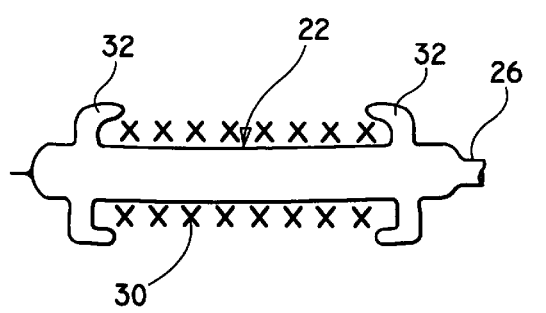
FIG. 2 is a schematic, side sectional view of the balloon catheter, according to a second embodiment of the invention.

The number and shape of the cuffs 28 may vary, as shown in FIGS. 2–5, depending on the specific application for which the stent will be implanted. FIG. 2 shows a configuration in which the balloon 22 is provided with two L-shaped cuffs 32. The L-shaped cuffs 32 have legs which extend toward one another and function to capture the stent 30 underneath and between the two legs.

Figure 3:
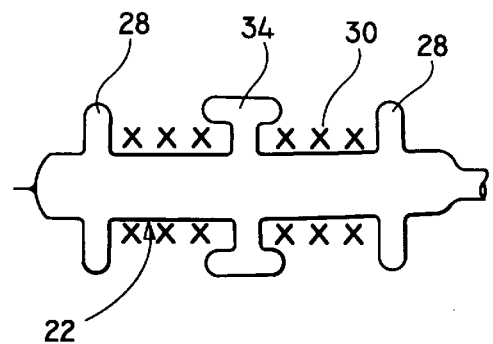
FIG. 3 is a schematic, side sectional view of the balloon catheter, according to a third embodiment of the invention.
Figure 4:
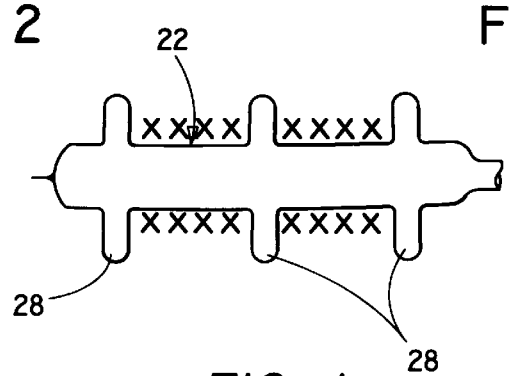
FIG. 4 is a schematic, side sectional view of the balloon catheter, according to a fourth embodiment of the invention.

According to the configuration of the invention shown in FIG. 3, three cuffs are used to retain and deploy two smaller stents. The two outside cuffs 28 are shaped as annular rings while the central cuff 34 has a T-shaped cross section which is used to maintain the stents 30 in place within the spaces between the cuffs. FIG. 4 shows a configuration in which three cuffs 28, each having the same configuration, are used to deploy a series of two stents. The cuff shapes shown in the drawings are merely examples of some of the cuff shapes which may be used in the present invention. Other shapes and numbers of cuffs may be used depending on the specific application.

The dimensions of the cuffs shown in FIGS. 2–5 have been exaggerated for purposes of explanation. However, the height of the cuffs may be as small as or slightly smaller than the thickness of the stent used. Stents which are suitable for use with the present invention include any stent which is substantially cylindrical and is balloon expandable.

The cuffs are preferably formed of a relatively soft and flexible material, such as, very thin plastic normally used for angioplasty balloons. Preferably, the cuffs are formed integrally with, and from the same material as the balloon. Once the cuffs are formed, they are heat set to retain their shape during sterilization and protracted shelf life. The heat setting procedure for the cuffs is similar to the heat setting processes which are known for setting the folds in balloons to promote low deflated profiles.

Figure 5:
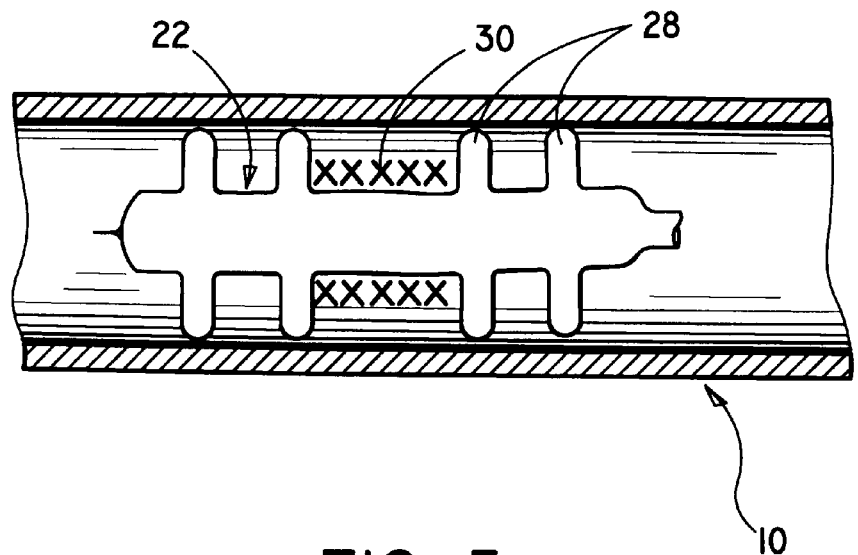
FIG. 5 is a schematic, side sectional view of the balloon catheter, according to a fifth embodiment of the invention, which is being inserted by a guide catheter.

The cuffs 28 do not interfere with the ability of the balloon to be pushed through the introducing catheter 10. As shown in FIG. 5, the cuffs actually provide the additional advantage of centering the balloon 20 and stent 30 within the introducing catheter 10 which facilitates the travel of the balloon through the catheter. In addition, if it is necessary for the stenting operation to be aborted, then the withdrawal of the system is facilitated by the proximal cuff which leads the stent and balloon back into the introducing catheter. This prevents the stent 30 from being dislodged from the balloon by the distal end of the introducing catheter. As shown in FIG. 5, a longer balloon having a plurality of cuffs can be used to selectively position a stent 30 on a distal, central, or proximal portion of the balloon 20. This configuration could also be used to hold multiple stents relative to each other in a modular fashion to create a long stent. The width of the cuffs can be modified to minimize the unsupported gaps between adjacent unconnected modular stents.

In operation, the balloon catheter 20 having a stent 30 positioned on the balloon 22 between the two cuffs 28, is inserted into the body through the tubular introducing catheter 10. The balloon catheter is guided by a guide wire which is positioned in the inner conduit 24 or by any other known guiding technique, to a desired location within a body lumen 40. The balloon 22 is then expanded by an inflation medium passing through the outer conduit 26. The balloon 22 continues to be inflated until the stent 30 engages the walls of the lumen 40. As the balloon is expanded, the cuffs 28 disappear into the wall of the balloon. When the balloon is then deflated for removal, the cuffs do not reappear and the catheter can be easily removed.

Figure 6:
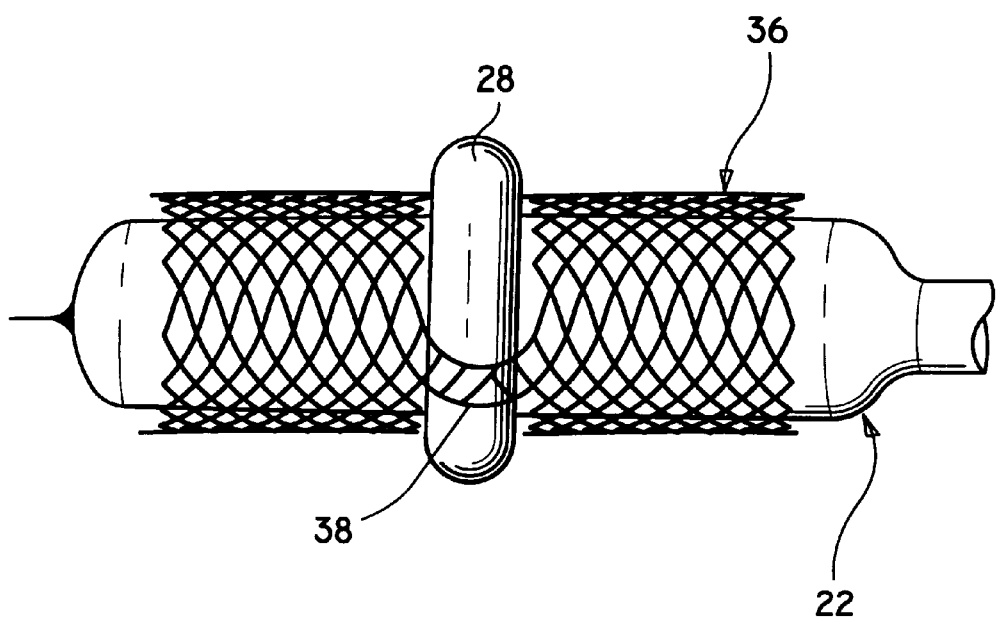
FIG. 6 is a side view of the balloon catheter, according to a sixth embodiment of the invention.
Figure 7A:
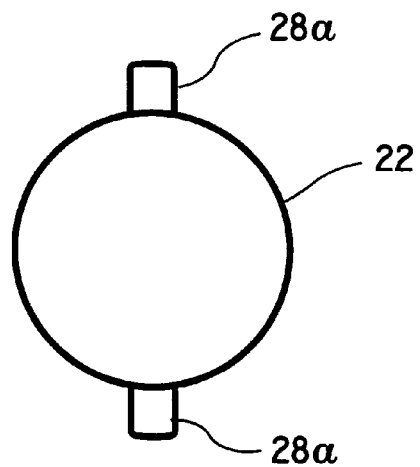
FIGS. 7 a–d show cross-sections of various configurations of projections in accordance with the invention.
Figure 7B:
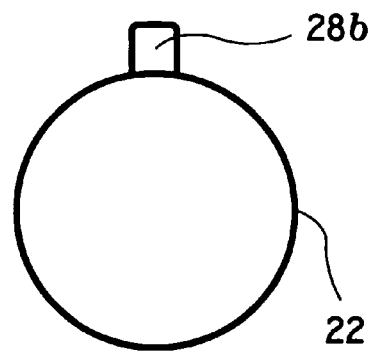
Figure 7C:
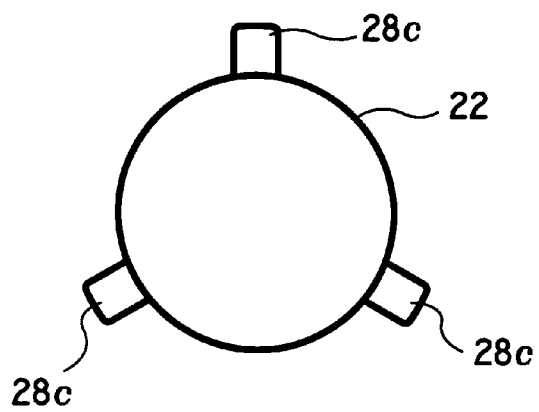
Figure 7D:
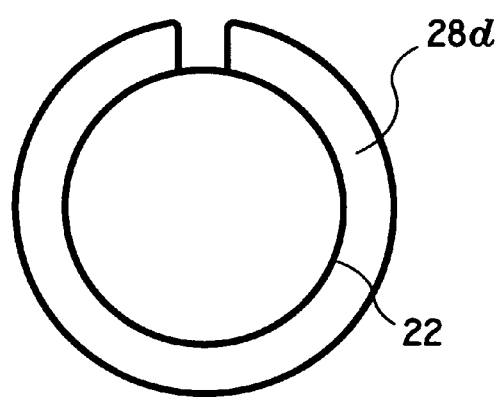

According to an alternative embodiment of the present invention shown in FIG. 6, an articulated stent 36 is positioned on a balloon 22 having a single cuff 28. The articulated stent 36 includes two expandable stents which are held together with a bridge element 38. The single cuff 28 is formed at the articulation site of the articulated stent 36 and the stent is held in place on the balloon by the bridge element 38 extending across the cuff. Alternatively, the cuff can be C-shaped to allow the bridge element 38 to extend through the opening of the C-shaped protrusion or the bridge element can extend through a space between a pair of projections spaced circumferentially around the balloon.

FIGS. 7 a–d show alternative configurations of the protrusion according to the invention. For instance, the protrusion can comprise a pair of protrusions 28a as in FIG. 7a, a single protrusion 28b as in FIG. 7b, three circumferentially spaced-apart protrusions 28c as in FIG. 7c or a C-shaped protrusion 28d as in FIG. 7d.

The cuffs 28 on the balloon 22 of the present invention may be formed by any one of a variety of different methods. One example of a method for forming the cuffs is described below. The balloon catheter 20 is fully formed, folded and heat set according to a conventional method. A first tubular cuff forming sleeve is slid over the balloon from the distal end of the balloon and positioned with the distal end of the first forming sleeve marking the location of the proximal retaining cuff. A stent is then slid over the exposed portion of the balloon leaving a small gap between the stent and the distal end of the first forming sleeve. A second tubular cuff forming sleeve is then positioned over the stent and over the entire distal end of the balloon. An annular gap is formed between the first and second forming sleeves. The balloon is then inflated to form the cuff in the annular region between the first and second forming sleeves. The cuff is held between the two forming sleeves while the balloon is deflated by aspiration of the inflation medium within the balloon. The second forming sleeve is then removed.

The second or distal cuff is then formed by sliding the first forming sleeve distally over the proximal cuff and the stent to the distal cuff site. A third forming sleeve is then placed on the distal end of the balloon to form an annular gap between the first and third forming sleeves in which to create the distal cuff. The second cuff is then formed in the same manner as the first cuff by inflating the balloon, holding the cuff with the forming sleeves, deflating the balloon, and removing the third forming sleeve. The first forming sleeve is advanced over the distal cuff and can remain in place as part of the final assembly whereby the sleeve protects the balloon and the stent as well as helps to maintain the protrusion configuration. The cuffs are then thermally set to retain the formed configuration.

The heat setting step which is performed to set the cuffs is similar to the heat setting process used to create the folds in the balloon. An example of an appropriate heat setting step includes heating in an oven at approximately 42° C. for three or four hours. The forgoing method has been set forth as an example of a process for forming the cuffs of the present invention. However, the cuffs may also be formed by other suitable methods using other types of sizing and shaping devices and alternative shape setting methods.

While the invention has been described in detail with reference to a preferred embodiment thereof, it will be apparent to one skilled in the art that various changes can be made, and equivalents employed without departing from the spirit and scope of the invention.

What is claimed is:

1. A balloon delivery system for deploying a stent within a tubular body lumen comprising:

an expandable balloon configured to receive a stent for maintaining an inside diameter of a lumen;

a passage in a tube in fluid communication with the expandable balloon;

at least one protrusion formed on an exterior of the balloon for securing the stent on the balloon during delivery and deployment of the stent within the lumen, the at least one protrusion being formed from the same material as the balloon, the at least one protrusion being formed of a flexible plastic material, the protrusion being transformed from a protruding configuration to a non-protruding configuration upon inflation of the balloon and the protrusion retaining the non-protruding configuration upon subsequent deflation of the balloon.

2. The balloon delivery system according to claim 1, wherein the at least one protrusion is formed integral with an expandable portion of the balloon.

3. The balloon delivery system according to claim 1, wherein the at least one protrusion has an L-shape in cross section.

4. The balloon delivery system according to claim 3, wherein the at least one protrusion comprises two annular cuffs which are L-shaped in cross section and the L-shaped cuffs are oriented such that extending legs of the cuffs extend toward one another.

5. The balloon delivery system according to claim 1, wherein the at least one protrusion comprises two annular cuffs and the balloon includes a space between the cuffs adapted for a stent to be positioned on the balloon.

6. The balloon delivery system according to claim 1, wherein the at least one protrusion comprises three annular spaced-apart cuffs, at least two stents being positioned on the balloon within spaces between the cuffs.

7. The balloon delivery system according to claim 1, wherein the at least one protrusion has a T-shaped cross section.

8. The balloon delivery system according to claim 1, wherein the at least one protrusion is heat treated to set a shape of the protrusion so that the protrusion shape is retained during sterilization and protracted shelf life.

9. The balloon delivery system according to claim 1, wherein the at least one protrusion comprises at least two annularly spaced-apart projections.

10. The balloon delivery system according to claim 1, wherein the at least one protrusion comprises a C-shaped ring.

11. A balloon delivery system for deploying a stent to maintain an inside diameter of a lumen, the system comprising:

an expandable balloon;

an expandable stent positioned on the balloon;

a tube connected to the balloon for inflating the balloon;

at least one protrusion formed on an exterior of the balloon securing the stent on the balloon, the at least one protrusion being formed from the same material as the balloon, the at least one protrusion being formed of a flexible plastic material, the protrusion being transformed from a protruding configuration to a non-protruding configuration upon inflation of the balloon and the protrusion retaining the non-protruding configuration upon subsequent deflation of the balloon.

12. The balloon delivery system according to claim 11, wherein the at least one protrusion is formed from the same material as the balloon.

13. The balloon delivery system according to claim 11, wherein the at least one protrusion is formed integral with an expandable portion of the balloon.

14. The balloon delivery system according to claim 11, wherein the at least one of the protrusion is L-shaped in cross section.

15. The balloon delivery system according to claim 11, wherein the at least one protrusion comprises two spaced-apart annular cuffs which are L-shaped in cross section and the L-shaped cuffs are oriented such that extending legs of the cuffs extend toward one another.

16. The balloon delivery system according to claim 11, wherein the at least one protrusion comprises three spaced-apart annular cuffs, the balloon is provided with three cuffs and includes spaces between the cuffs, at least two stents being positioned on the balloon within spaces between the cuffs.

17. The balloon delivery system according to claim 11, wherein the at least one protrusion has a T-shaped cross section.

18. The balloon delivery system according to claim 11, wherein the at least one protrusion is heat treated to set a shape of the protrusion so that the protrusion shape is retained during sterilization and protracted shelf life.

19. The balloon delivery system according to claim 11, wherein the at least one protrusion comprises at least two annularly spaced-apart projections.

20. The balloon delivery system according to claim 11, wherein the at least one protrusion comprises a C-shaped ring.

21. The balloon delivery system according to claim 11, wherein the stent is a substantially cylindrical member which is positioned adjacent the at least one protrusion.

22. A method of deploying a stent within a body lumen with a balloon catheter, the balloon catheter including a balloon having at least one protrusion for securing the stent in place on the balloon, the method comprising the steps of:

positioning a stent adjacent said at least one protrusion on the balloon catheter;

inserting the balloon catheter and stent into a body through a tubular catheter;

positioning the stent within a body lumen;

deploying the stent by inflating the balloon;

deflating the balloon; and removing the balloon and the catheter from the body, the at least one protrusion being formed from the same material as the balloon, and the protrusion becoming non protruding upon inflation of the balloon.

23. The method of deploying a stent of claim 22, wherein the at least one protrusion comprises two spaced-apart annular cuffs, the step of positioning the stent including positioning the stent between the two cuffs on the balloon.

24. The method of deploying a stent of claim 22, wherein the at least one protrusion comprises three spaced-apart annular cuffs, the stent being positioned between one pair of the cuffs and an additional stent being positioned between another pair of the cuffs, the stents being deployed by inflating the balloon.

25. A balloon delivery system for deploying a stent within a tubular body lumen comprising:

an expandable balloon having at least one protrusion formed on an exterior of the balloon; and an articulated expandable stent positioned on the balloon, the stent including two substantially cylindrical portions connected by a bridge element, the bridge element cooperating with the at least one protrusion to secure the stent on the balloon, the at least one protrusion being formed from the same material as the balloon, and the protrusion becoming non-protruding upon inflation of the balloon.

26. A balloon for deploying a stent within a body lumen comprising:

an expandable balloon configured to receive a stent for maintaining an inside diameter of a lumen;

the balloon having a pre-inflated state, wherein protrusions extending from the balloon protrude radially to secure the stent to the balloon;

the balloon having an inflated state, wherein the protrusions extending from the balloon transform from a protruding configuration to a non-protruding configuration; and the balloon having a deflated state, wherein the protrusions are in the non-protruding configuration.

* * * * *